(12) United States Patent
Lorden

(10) Patent No.: US 10,390,771 B2
(45) Date of Patent: Aug. 27, 2019

(54) SAFETY MONITORING WITH WEARABLE DEVICES

(71) Applicant: Zoi Inc., Los Angeles, CA (US)

(72) Inventor: Bryan Alexander Lorden, Los Angeles, CA (US)

(*) Notice: Subject to any disclaimer, the term of this patent is extended or adjusted under 35 U.S.C. 154(b) by 192 days.

(21) Appl. No.: 15/413,170

(22) Filed: Jan. 23, 2017

(65) Prior Publication Data

US 2018/0055456 A1    Mar. 1, 2018

Related U.S. Application Data

(60) Provisional application No. 62/379,334, filed on Aug. 25, 2016.

(51) Int. Cl.
| | | |
|---|---|---|
| *A61B 5/00* | (2006.01) | |
| *G09B 5/02* | (2006.01) | |
| *A61B 5/024* | (2006.01) | |
| *G09B 23/28* | (2006.01) | |
| *G16H 50/30* | (2018.01) | |

(52) U.S. Cl.
CPC .......... *A61B 5/746* (2013.01); *A61B 5/0004* (2013.01); *A61B 5/024* (2013.01); *A61B 5/681* (2013.01); *A61B 5/7246* (2013.01); *A61B 5/7275* (2013.01); *A61B 5/7282* (2013.01); *A61B 5/742* (2013.01); *G09B 5/02* (2013.01); *G09B 23/28* (2013.01); *G16H 50/30* (2018.01)

(58) Field of Classification Search
CPC ....... A61B 5/746; A61B 5/742; A61B 5/0004; A61B 5/681; A61B 5/024; A61B 5/7282; G09B 2/02

See application file for complete search history.

(56) References Cited

U.S. PATENT DOCUMENTS

| | | |
|---|---|---|
| 5,228,449 A | 7/1993 | Christ et al. |
| 5,348,008 A | 9/1994 | Bornn et al. |
| 5,544,649 A | 8/1996 | David et al. |
| 7,148,797 B2 | 12/2006 | Albert |
| 7,154,398 B2 | 12/2006 | Chen et al. |
| 7,301,451 B2 | 11/2007 | Hastings |
| 9,083,997 B2 | 7/2015 | Harwell et al. |
| 9,314,159 B2 | 4/2016 | Lyon et al. |
| 9,339,663 B2 | 5/2016 | Sullivan et al. |
| 2005/0148890 A1 | 7/2005 | Hastings |
| 2007/0027367 A1 | 2/2007 | Oliver |

(Continued)

*Primary Examiner* — Catherine M Voorhees
*Assistant Examiner* — Roland Dinga
(74) *Attorney, Agent, or Firm* — Carlos R. Perez-Toro

(57) ABSTRACT

Disclosed herein are system, method, and computer program product embodiments for detecting an irregularity in a user's vital signs and alerting of a potential emergency using wearable devices. An embodiment operates by receiving, from a sensor component coupled to a wearable computing device, real-time heart rate information associated with a user wearing the wearable computing device. The system accesses heart rate calibration information associated with a user profile and detects an irregularity based on a comparison between the real-time heart rate information and the heart rate calibration information. Based on the detected irregularity, the system accesses a contact information associated with the user profile and transmits a message based on the contact information.

20 Claims, 4 Drawing Sheets

(56) References Cited

U.S. PATENT DOCUMENTS

| | | | |
|---|---|---|---|
| 2009/0322513 A1* | 12/2009 | Hwang | A61B 5/02055 340/539.12 |
| 2012/0203076 A1* | 8/2012 | Fatta | A61B 5/681 600/300 |
| 2013/0172691 A1 | 7/2013 | Tran | |
| 2014/0073486 A1 | 3/2014 | Ahmed et al. | |
| 2016/0174857 A1 | 6/2016 | Eggers et al. | |

* cited by examiner

SAFETY MONITORING WITH WEARABLE DEVICES

BACKGROUND

Technical Field

Embodiments generally relate to monitoring the safety and health of a person using wearable devices.

BACKGROUND

Certain medical conditions may cause sudden symptoms in unpredictable manners. For example, elderly individuals with heart conditions may benefit from 24-hour monitoring to treat unexpected symptoms that can occur, such as a heart failure during sleep. Persons in this situation may not be able to call for help, and may not even realize that they are having an emergency.

Wearable computing devices may be useful in monitoring a user's health in a real-time or nearly real-time basis. For example, some electronic watches may monitor and record data associated with a user's heart rate. These devices may also enable anyone to track their health closely, including those in good health or with minor conditions.

SUMMARY

Disclosed herein are system, method, and computer program product embodiments for detecting an irregularity in a user's vital signs and alerting of a potential emergency using wearable devices. An embodiment operates by receiving, from a sensor component coupled to a wearable computing device, real-time heart rate information associated with a user wearing the wearable computing device. The system accesses heart rate calibration information associated with a user profile and detects an irregularity based on a comparison between the real-time heart rate information and the heart rate calibration information. Based on the detected irregularity, the system accesses a contact information associated with the user profile and transmits a message based on the contact information.

The embodiments disclosed above are only examples, and the scope of this disclosure is not limited to them. Particular embodiments may include all, some, or none of the components, elements, features, functions, operations, or steps of the embodiments disclosed above. Embodiments according to the invention are in particular disclosed in the attached claims directed to a method, a storage medium, a system and a computer program product, wherein any feature mentioned in one claim category, e.g. method, can be claimed in another claim category, e.g. system, as well. The dependencies or references back in the attached claims are chosen for formal reasons only. However any subject matter resulting from a deliberate reference back to any previous claims (in particular multiple dependencies) can be claimed as well, so that any combination of claims and the features thereof are disclosed and can be claimed regardless of the dependencies chosen in the attached claims. The subject-matter which can be claimed comprises not only the combinations of features as set out in the attached claims but also any other combination of features in the claims, wherein each feature mentioned in the claims can be combined with any other feature or combination of other features in the claims. Furthermore, any of the embodiments and features described or depicted herein can be claimed in a separate claim and/or in any combination with any embodiment or feature described or depicted herein or with any of the features of the attached claims.

BRIEF DESCRIPTION OF THE DRAWINGS

The accompanying drawings are incorporated herein and form a part of the specification.

In the drawings, like reference numbers generally indicate identical or similar elements. Additionally, generally, the left-most digit(s) of a reference number identifies the drawing in which the reference number first appears.

DETAILED DESCRIPTION

Provided herein are system, method and/or computer program product embodiments, and/or combinations and sub-combinations thereof, for detecting an irregularity in a user's vital signs and alerting of a potential emergency.

Figure 1:
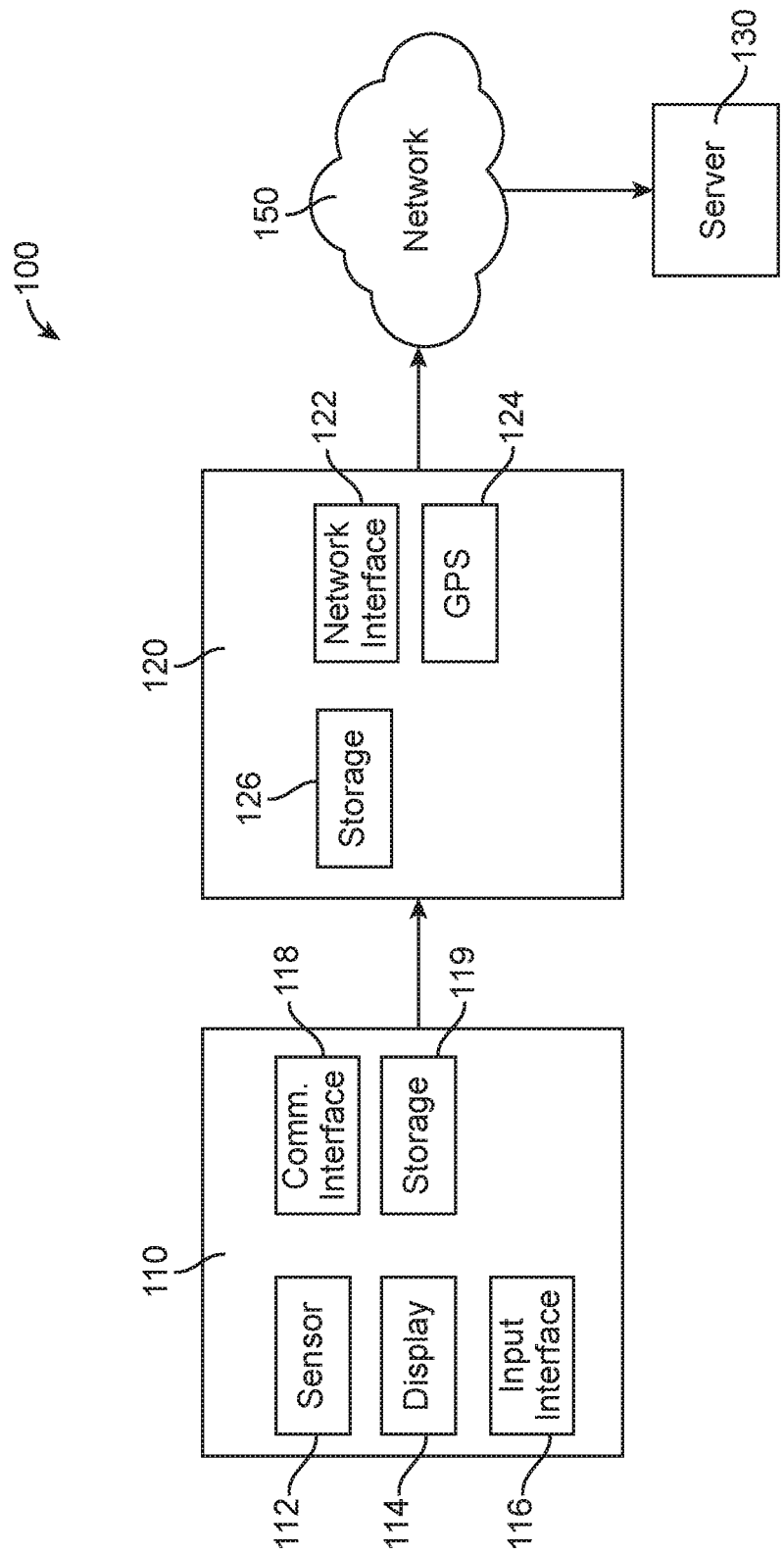
FIG. 1 illustrates a health-monitoring environment, according to an example embodiment.

FIG. 1 illustrates a health-monitoring environment 100, according to an example embodiment. A wearable computing device 110 may include a sensor component 112, a display 114, an input interface 116, a communications interface 118, and a storage 119. In an embodiment, wearable computing device 110 is a smartwatch including a visual display and a heart rate sensor component. In an embodiment, wearable computing device 110 may comprise any suitable wearable device, such as a vest, earbuds, stick-on-skin sensors, bracelet, clothing, hat, etc., including a sensor for any vital signs, such as heart rate, breathing, heart pressure, blood sugar, movement patterns, sleep patterns, snoring, temperature, etc.

A user may wear wearable computing device 110 during particular activities or at all times. Wearable computing device 110 may measure the user's vital signs and transmit sensor reading data to processing component 120. Processor component 120 may analyze the data to detect irregularities. Wearable computing device 110 may communicate with processing component 120 through communications interface 118. Processing component 120 may be any device configured to process sensor data from sensor component 112 such as, by way of example, a personal computer, mobile computer, laptop computer, mobile phone, smartphone, personal digital assistant, or tablet computer. In an example embodiment, processing component 120 may be a smartphone in communication with wearable computing device 110 through a wireless connection (e.g., Bluetooth, WiFi, etc.), and configured to process sensor data through a software application. In particular embodiments, some or all the functions of processing component 120 described throughout this disclosure may be integrated within wearable computing device 110, for example, as an application running on computing hardware within wearable computing device 110.

Processing component 120 may determine whether vital signs sensor data from sensor component 112 indicate normal activity or some irregularity associated with medical conditions. Processing component 120 may include a storage 126 that stores calibration information associated with the user that is compared to sensor readings to detect irregular vital signs patterns. In an embodiment, processing component 120 may communicate with a cloud or server system 130 for performing data processing. Server system 120 may be any computing device or combination of devices suitable to provide server functionalities, such as, by way of example, server computers, database systems, storage area networks, web servers, application servers, or any combination thereof. While the rest of this disclosure describes the processing device 120 as performing certain functions, it should be understood that the processing device 120 may perform these functions in collaboration with one or more server devices 130. As an example, processing device 120 may send some, all, or a summary of sensor data to a server device 130 for enhanced processing and irregularity detection.

If an emergency condition is detected through the data processing, processing component 120 may send an alert to the user and people that may be able to assist the user, for example, first responders, family members, doctors, nurses, etc. Alerts and messages may be sent through any suitable means of communication, such as, Short Message Service (SMS), e-mail, voice calls, etc. Processing component 120 may include a network interface 122 for transmitting data through a communications network 150. As an example, network interface 122 may be a wireless communication interface (e.g., WiFi, cellular networking interface, etc.), wired (e.g., Ethernet, phone landline, etc.), or any combination thereof. The network 150 may be any communications network suitable for transmitting data between computing devices, such as, by way of example, a Local Area Network (LAN), a Wide Area Network (WAN), Metropolitan Area Network (MAN), Personal Area Network (PAN), the Internet, wireless networks, satellite networks, overlay networks, cellular networks, or any combination thereof.

In an embodiment, wearable device 110, processing device 120, or both, may include a Global Positioning System (GPS) module 124 for determining a location of the user. In this manner, processing device 120 may determine a location of the user to include in an alert, thus letting other know where the person with the emergency is located.

Figure 2:
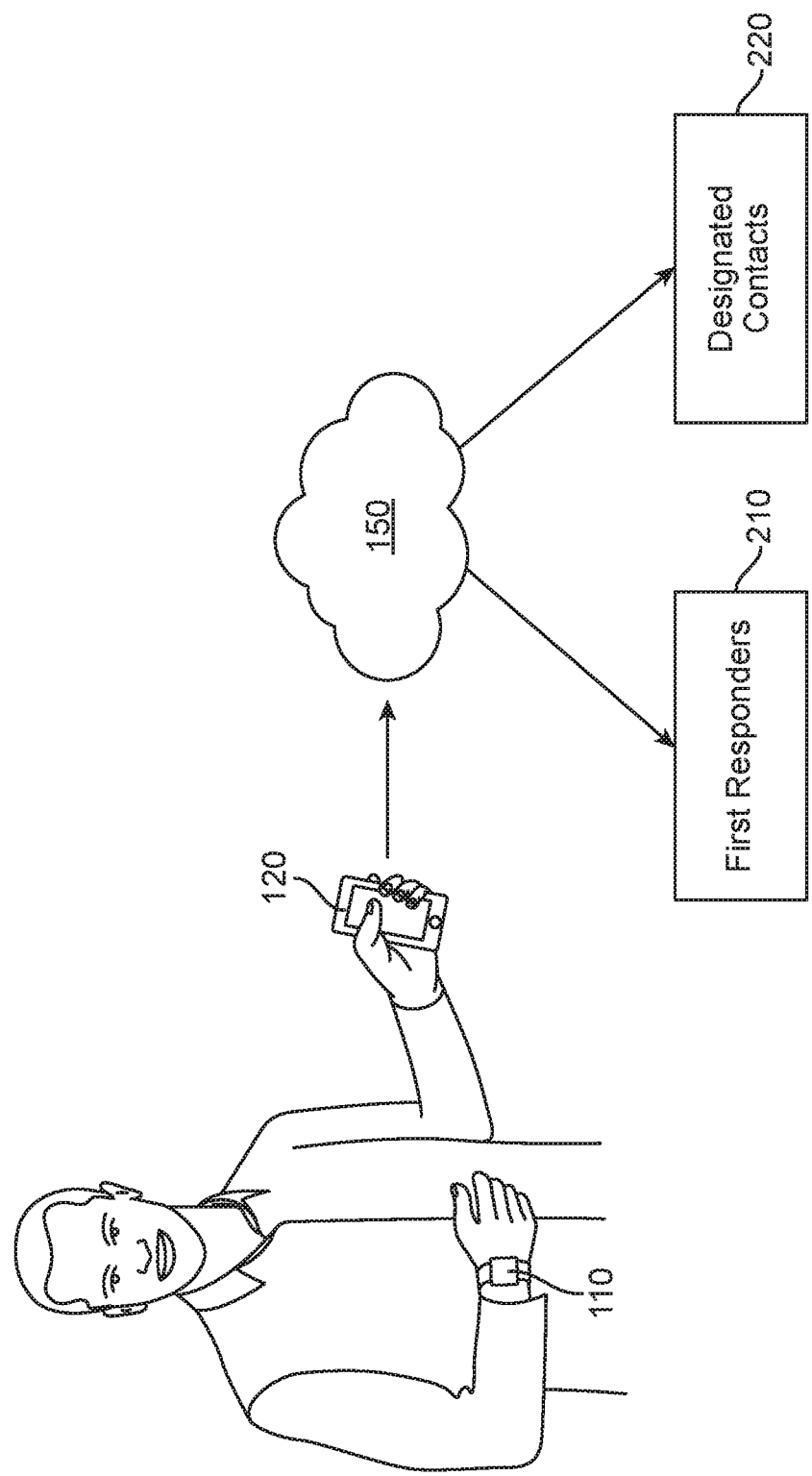
FIG. 2 illustrates a block diagram describing the functionality of a health-monitoring system, according to an example embodiment.

FIG. 2 illustrates a block diagram describing the functionality of a health-monitoring system, according to an example embodiment. Wearable device 110 may first be configured to understand what a user's regular or normal vital sign patterns are. In an embodiment, a user may wear wearable device 110 during a calibration/training phase, where wearable computing device 110 transmits vital sign sensor data to processing device 120, which then generates a calibration data profile for the user. For example, a user may wear the wearable computing device 110 while sleeping, and the processing device 120 may generate a heart-beat profile for the user while sleeping. A heart-beat profile may include, for example, a measure of beats-per-minute (bpm), a heart rhythm, blood pressure, etc. In an embodiment, the processing device 120 may continuously learn the user's patterns over time as the user wears the wearable computing device 110, and periodically adjust the calibration data.

In an embodiment, the calibration data profile includes data associated with a particular activity. As an example, the wearable computing device 110, the processing device 120, or both, may allow the user to enter an activity that they are or will be performing (e.g., resting, exercising, working, sleeping, etc.). Processing device 120 may then learn the user's normal pattern for that activity, and include associated data in the calibration data.

In an embodiment, the calibration data profile includes data associated with the time of the day. For example, processing device 120 may detect that a user regularly has a heart rate of 70 bpm between 10:00 PM-6:00 AM (e.g., the user regularly in bed during those times of the day). Thus, processing device 120 may reflect this in the calibration data.

Once the calibration data profile is created, the processing device 120 monitors the sensor readings in real-time to detect any irregularities. In an embodiment, real-time monitoring may be performed by monitoring the vital signs at a regular periodic interval (e.g., every thirty seconds, one minute, five minutes, etc.). In an embodiment, sensor data is sent continuously to processing device 120. In an embodiment, processing device 120 may monitor data at a regular interval, and may then decrease the length of the interval if an irregularity is detected in order to obtain more accurate data.

In an embodiment, processing device 120 detects an irregularity when sensor readings deviate from the calibration data by more than a configurable threshold. In an embodiment, this threshold is adjustable by the user (e.g., trigger an alarm if bpm is above or below 20 bpm from the average for this activity). In an embodiment, the threshold is expressed as a number of standard deviations away from the calibration data.

In an embodiment, wearable computing device 110, processing device 120, or both, allow a user to input an activity she is about to perform (e.g., resting, exercising, working, sleeping, etc.) Processing device 120 may then compare the sensor readings to the corresponding calibration data for that activity. Similarly, processing device 120 may compare the sensor readings for calibration data associated with the time of day.

In an embodiment, wearable computing device 110, processing device 120, or both, may actuate an alarm or notification for the user wearing the wearable device when an irregularity is detected. The notification may be an audible, visual, and/or tactile notification. For example, wearable computing device 110 may provide a notification to the user asking to confirm or cancel an emergency notification (e.g., "Are you having a medical emergency? Press Yes to confirm, No to cancel.") In this manner, processing device 120 may assess whether the user is actually having an emergency or its irregularity detection is a false alarm. In an embodiment, if the user does not respond to the alert within a configurable amount of time, the processing device 120 assumes the emergency is real and proceeds to the emergency alert phase.

If processing device 120 detects an irregularity, processing device 120 may issue an alert to emergency responders 210 or designated contacts 220. For example, processing device 120 may issue a message to paramedics or emergency management technicians (EMTs) with information about the user and the emergency. For example, the message may contain identifying information (e.g., name, age, physical description), a location, and background medical information (e.g., allergies, medical conditions, etc.) In an embodiment, the message may also include technical information associated with the irregularity detected, such as a description of the nature of the emergency (e.g., "Possible heart attack," "Possible stroke," "heart rate of 190 bpm," "No pulse," "irregular heart-beat," "tachycardia," etc.). In an embodiment, processing device 120 may send an alert to designated contacts 220, such as family members, nurses, doctors, etc. In an embodiment, processing device 120 may include instructions in the message (e.g., "call paramedics," "elevate legs," "perform CPR.") In an embodiment, the message may also include instructions on how to perform necessary first aid, such as cardiopulmonary resuscitation (CPR).

In an embodiments, wearable computing device 110, processing device 120, or both, may trigger an audible and/or visual alert for people in proximity to the user. For example, wearable computing device 110 may audibly sound an alarm and play a voice stating "the person wearing this watch needs help." In an embodiment, the alert may include displaying information that may help others assist the user, or may assist first responder in treating the users, such as information on the nature of the emergency, the user's vital sign, how to perform first aid, etc.

In an embodiment, processing device 120 may detect and alert the user of non-emergency irregularities. As an example, if the user has a mild irregular heartbeat, processing device 120 may alert the user that she should be checked by a doctor in a regular appointment.

In an embodiment, processing device 120 may provide a periodical summary of the user's vital signs measurements over a period of time. As an example, processing device 120 may provide a weekly report stating the user's average resting heart rate, sleeping heart rate, jogging heart rate, etc. In an embodiment, the summary may include recommendations, alert the user to potential health problems, etc.

Figure 3:
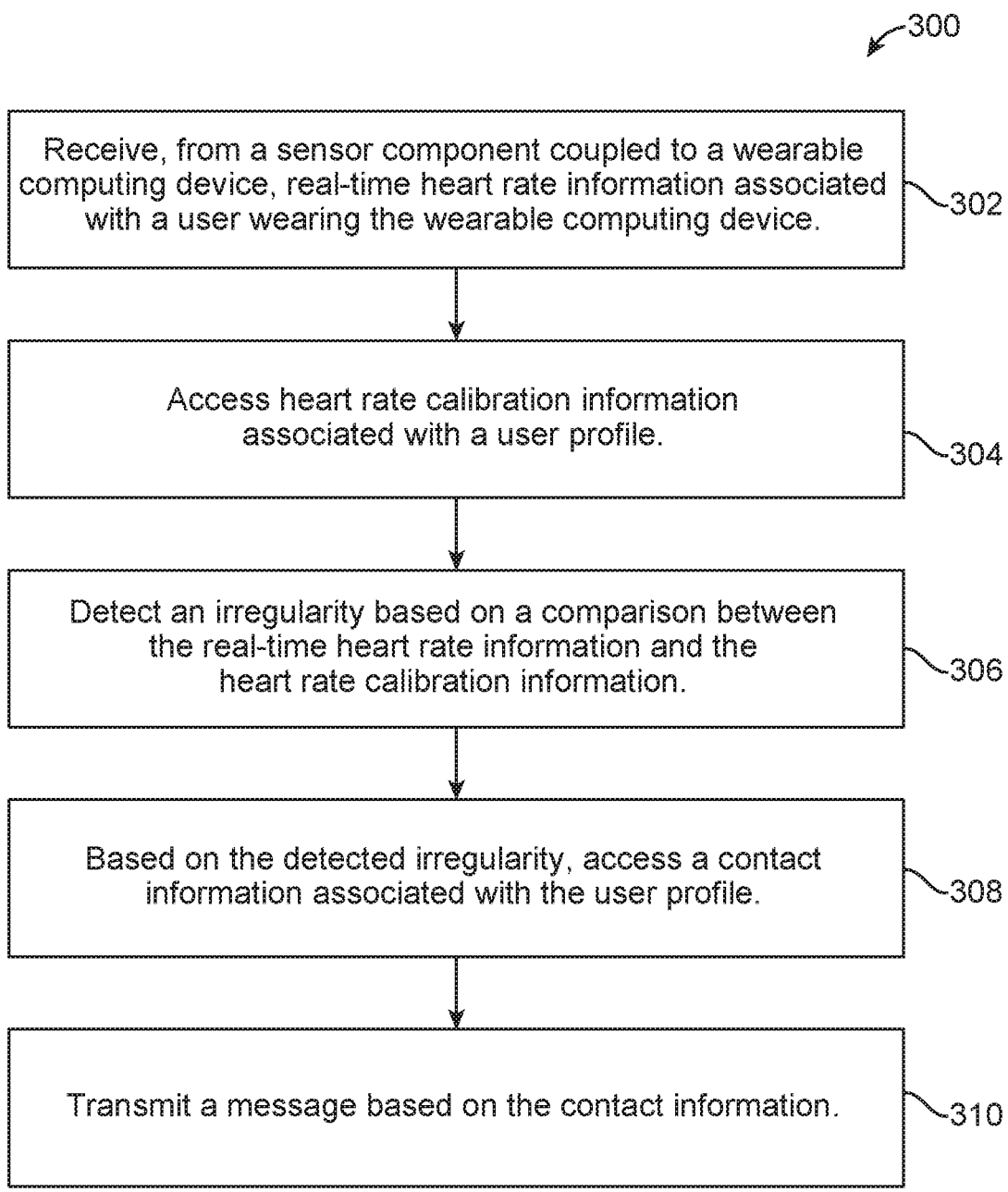
FIG. 3 is a flowchart for a method for detecting an irregularity in a user's vital signs and alerting of a potential emergency, according to an example embodiment.

FIG. 3 is a flowchart for a method 300 for detecting an irregularity in a user's vital signs and alerting of a potential emergency, according to an example embodiment. Method 300 can be performed by processing logic that can comprise hardware (e.g., circuitry, dedicated logic, programmable logic, microcode, etc.), software (e.g., instructions run on a processing device), or a combination thereof.

In step 302, processing device 120 receives, from a sensor component coupled to a wearable computing device, real-time heart rate information associated with a user wearing the wearable computing device. In step 304, processing device 120 accesses heart rate calibration information associated with a user profile. In step 306, processing device 120 detects an irregularity based on a comparison between the real-time heart rate information and the heart rate calibration information. In step 308, processing device 120, based on the detected irregularity, accesses a contact information associated with the user profile. In step 310, processing device 120 transmits a message based on the contact information.

Figure 4:
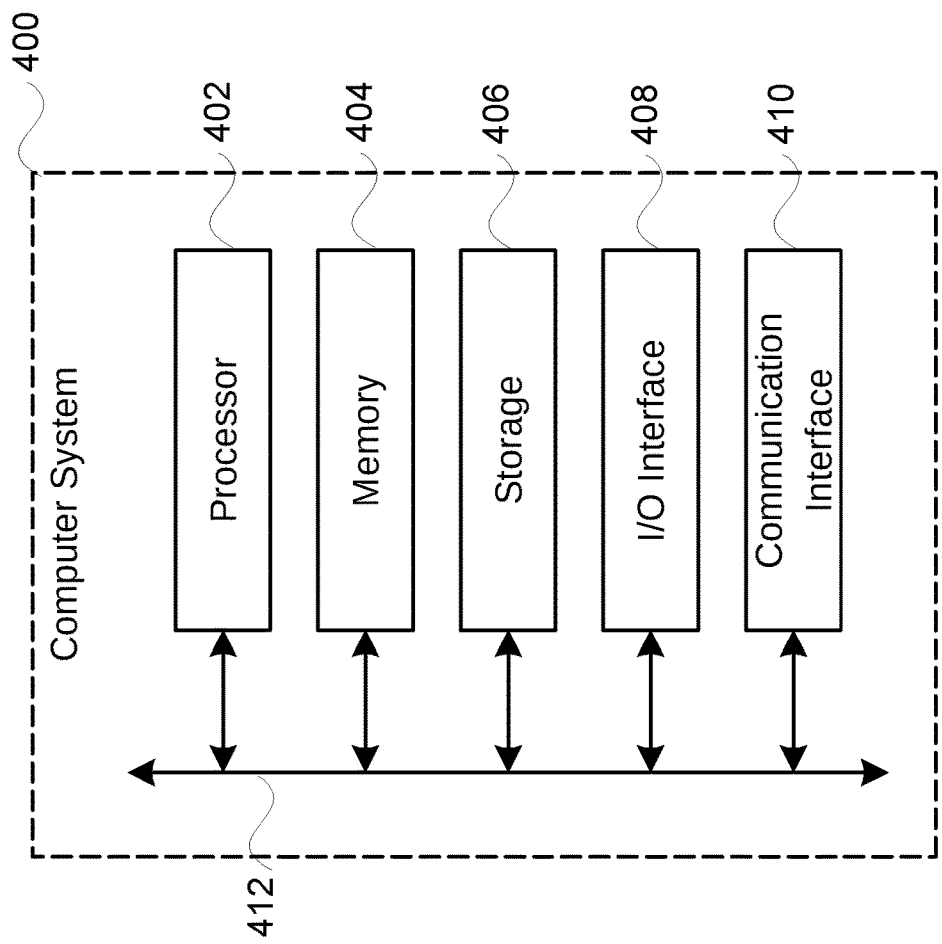
FIG. 4 is an example computer system useful for implementing various embodiments.

FIG. 4 illustrates an example computer system 400. In particular embodiments, one or more computer systems 400 perform one or more steps of one or more methods described or illustrated herein. In particular embodiments, one or more computer systems 400 provide functionality described or illustrated herein. In particular embodiments, software running on one or more computer systems 400 performs one or more steps of one or more methods described or illustrated herein or provides functionality described or illustrated herein. Particular embodiments include one or more portions of one or more computer systems 400. Herein, reference to a computer system may encompass a computing device, and vice versa, where appropriate. Moreover, reference to a computer system may encompass one or more computer systems, where appropriate.

This disclosure contemplates any suitable number of computer systems 400. This disclosure contemplates computer system 400 taking any suitable physical form. As example, computer system 400 may be an embedded computer system, a desktop computer system, a laptop or notebook computer system, a mainframe, a mobile telephone, a personal digital assistant (PDA), a server, a tablet computer system, or a combination of two or more of these. Where appropriate, computer system 400 may include one or more computer systems 400; be unitary or distributed; span multiple locations; span multiple machines; span multiple data centers; or reside in a cloud, which may include one or more cloud components in one or more networks. Where appropriate, one or more computer systems 400 may perform without substantial spatial or temporal limitation one or more steps of one or more methods described or illustrated herein. As an example, one or more computer systems 400 may perform in real time or in batch mode one or more steps of one or more methods described or illustrated herein. One or more computer systems 400 may perform at different times or at different locations one or more steps of one or more methods described or illustrated herein, where appropriate.

In particular embodiments, computer system 400 includes a processor 402, memory 404, storage 406, an input/output (I/O) interface 408, a communication interface 410, and a bus 412. Although this disclosure describes and illustrates a particular computer system having a particular number of particular components in a particular arrangement, this disclosure contemplates any suitable computer system having any suitable number of any suitable components in any suitable arrangement.

In particular embodiments, processor 402 includes hardware for executing instructions, such as those making up a computer program. As an example, to execute instructions, processor 402 may retrieve (or fetch) the instructions from an internal register, an internal cache, memory 404, or storage 406; decode and execute them; and then write one or more results to an internal register, an internal cache, memory 404, or storage 406. In particular embodiments, processor 402 may include one or more internal caches for data, instructions, or addresses. This disclosure contemplates processor 402 including any suitable number of any suitable internal caches, where appropriate. In particular embodiments, processor 402 may include one or more internal registers for data, instructions, or addresses. This disclosure contemplates processor 402 including any suitable number of any suitable internal registers, where appropriate. Where appropriate, processor 402 may include one or more arithmetic logic units (ALUs); be a multi-core processor; or include one or more processors 402. Although this disclosure describes and illustrates a particular processor, this disclosure contemplates any suitable processor.

In particular embodiments, memory 404 includes main memory for storing instructions for processor 402 to execute or data for processor 402 to operate on. As an example, computer system 400 may load instructions from storage 406 or another source (such as, for example, another computer system 400) to memory 404. Processor 402 may then load the instructions from memory 404 to an internal register or internal cache. To execute the instructions, processor 402 may retrieve the instructions from the internal register or internal cache and decode them. During or after execution of the instructions, processor 402 may write one or more results (which may be intermediate or final results) to the internal register or internal cache. Processor 402 may then write one or more of those results to memory 404. In particular embodiments, processor 402 executes only instructions in one or more internal registers or internal caches or in memory 404 (as opposed to storage 406 or elsewhere) and operates only on data in one or more internal registers or internal caches or in memory 404 (as opposed to storage 406 or elsewhere). One or more memory buses (which may each include an address bus and a data bus) may couple processor 402 to memory 404. Bus 412 may include one or more memory buses, as described below. In particular embodiments, memory 404 includes random access memory (RAM). This RAM may be volatile memory, where appropriate Memory 404 may include one or more memories 404, where appropriate. Although this disclosure describes and illustrates particular memory, this disclosure contemplates any suitable memory.

In particular embodiments, storage 406 includes mass storage for data or instructions. As an example, storage 406 may include a hard disk drive (HDD), a floppy disk drive, flash memory, an optical disc, a magneto-optical disc, magnetic tape, or a Universal Serial Bus (USB) drive or a combination of two or more of these. Storage 406 may include removable or non-removable (or fixed) media, where appropriate. Storage 406 may be internal or external to computer system 400, where appropriate. In particular embodiments, storage 406 is non-volatile, solid-state memory. In particular embodiments, storage 406 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 406 taking any suitable physical form. Storage 406 may include one or more storage control units facilitating communication between processor 402 and storage 406, where appropriate. Where appropriate, storage 406 may include one or more storages 406. Although this disclosure describes and illustrates particular storage, this disclosure contemplates any suitable storage.

In particular embodiments, I/O interface 408 includes hardware, software, or both, providing one or more interfaces for communication between computer system 400 and one or more I/O devices. Computer system 400 may include one or more of these I/O devices, where appropriate. One or more of these I/O devices may enable communication between a person and computer system 400. As an example, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 408 for them. Where appropriate, I/O interface 408 may include one or more device or software drivers enabling processor 402 to drive one or more of these I/O devices. I/O interface 408 may include one or more I/O interfaces 408, where appropriate. Although this disclosure describes and illustrates a particular I/O interface, this disclosure contemplates any suitable I/O interface.

In particular embodiments, communication interface 410 includes hardware, software, or both providing one or more interfaces for communication (such as, for example, packet-based communication) between computer system 400 and one or more other computer systems 400 or one or more networks. As an example, communication interface 410 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 410 for it. As an example, computer system 400 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 400 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 400 may include any suitable communication interface 410 for any of these networks, where appropriate. Communication interface 410 may include one or more communication interfaces 410, where appropriate. Although this disclosure describes and illustrates a particular communication interface, this disclosure contemplates any suitable communication interface.

In particular embodiments, bus 412 includes hardware, software, or both coupling components of computer system 400 to each other. As an example, bus 412 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 412 may include one or more buses 412, where appropriate. Although this disclosure describes and illustrates a particular bus, this disclosure contemplates any suitable bus or interconnect.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

It is to be appreciated that the Detailed Description section, and not the Summary and Abstract sections (if any), is intended to be used to interpret the claims. The Summary and Abstract sections (if any) may set forth one or more but not all exemplary embodiments of the invention as contemplated by the inventor(s), and thus, are not intended to limit the invention or the appended claims in any way.

While the invention has been described herein with reference to exemplary embodiments for exemplary fields and applications, it should be understood that the invention is not limited thereto. Other embodiments and modifications thereto are possible, and are within the scope and spirit of the invention. For example, and without limiting the generality of this paragraph, embodiments are not limited to the software, hardware, firmware, and/or entities illustrated in the figures and/or described herein. Further, embodiments (whether or not explicitly described herein) have significant utility to fields and applications beyond the examples described herein.

Embodiments have been described herein with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. Also, alternative embodiments may perform functional blocks, steps, operations, methods, etc. using orderings different than those described herein.

References herein to "one embodiment," "an embodiment," "an example embodiment," or similar phrases, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of persons skilled in the relevant art(s) to incorporate such feature, structure, or characteristic into other embodiments whether or not explicitly mentioned or described herein.

The breadth and scope of the invention should not be limited by any of the above-described exemplary embodiments, but should be defined only in accordance with the following claims and their equivalents.

What is claimed is:

1. A computer implemented method comprising, by at least one processor:
   receiving a user input for the creation of a user heart-beat profile associated with a user wearing a wearable computing device, wherein the user input further specifies a particular activity or time of day associated with the heart-beat profile;
   in response to the user input, monitoring real-time heart rate information over a period of time from a sensor component coupled to the wearable computing device;
   generating heart rate calibration information based on the monitoring;
   storing the heart rate calibration information in association with the particular activity or time of day;
   receiving, from the sensor component coupled to the wearable computing device, real-time heart rate information associated with the user;
   accessing the heart rate calibration information associated with the heart-beat profile;
   detecting an irregularity based on a comparison between the real-time heart rate information and the heart rate calibration information;
   based on the detected irregularity, accessing a contact information associated with a user profile; and
   transmitting a message based on the contact information.

2. The method of claim 1, wherein:
   the user input further specifies a particular activity or time of day associated with the heart-beat profile, wherein the particular activity may be at least one of resting, exercising, working, or sleeping.

3. The method of claim 1, wherein detecting an irregularity comprises detecting a heart rate that is above a threshold heart rate for a particular time of the day.

4. The method of claim 1, further comprising:
   determining the user wearing the wearable computing device is performing a particular activity,
   wherein the accessed heart rate calibration information depends on the particular activity.

5. The method of claim 4, wherein the particular activity is determined based on a time of the day.

6. The method of claim 4, wherein the particular activity is determined based on a user input.

7. The method of claim 4, wherein the particular activity is one of sleeping, exercising, or sitting.

8. The method of claim 4, wherein the particular activity is determined based on a time of the day.

9. The method of claim 1, further comprising:
   upon the detecting the irregularity, alerting the user of the wearable computing device through an interface functionality of the wearable computing device;
   wherein the transmitting the message based on the contact information is performed a predetermined period of time after alerting the user.

10. The method of claim 1, further comprising:
    displaying, on an interface of the wearable computing device, medical information associated with the user profile.

11. The method of claim 1, wherein the transmitting the message is performed by a smartphone in communication with the wearable computing device.

12. A system, comprising:
    a memory; and
    at least one processor coupled to the memory and configured to:
      receive a user input for the creation of a user heart-beat profile associated with a user wearing a wearable computing device, wherein the user input further specifies a particular activity or time of day associated with the heart-beat profile;
      in response to the user input, monitor real-time heart rate information over a period of time from a sensor component coupled to the wearable computing device;
      generate heart rate calibration information based on the monitoring;
      store the heart rate calibration information in association with the particular activity or time of day;
      receive, from the sensor component coupled to the wearable computing device, real-time heart rate information associated with the user;
      access the heart rate calibration information associated with a user the heart-beat profile;
      detect an irregularity based on a comparison between the real-time heart rate information and the heart rate calibration information;
      based on the detected irregularity, access a contact information associated with a user profile; and
      transmit a message based on the contact information.

13. The system of claim 12, wherein:
    the user input further specifies a particular activity or time of day associated with the heart-beat profile, wherein the particular activity may be at least one of resting, exercising, working, or sleeping.

14. The system of claim 12, wherein to detect an irregularity the at least one processor is configured to detect a heart rate that is above a threshold heart rate for a particular time of the day.

15. The system of claim 12, the at least one processor further configured to:
   determine the user wearing the wearable computing device is performing a particular activity,
   wherein the accessed heart rate calibration information depends on the particular activity.

16. The system of claim 15, wherein the particular activity is determined based on a time of the day.

17. A tangible computer-readable device having instructions stored thereon that, when executed by at least one computing device, causes the at least one computing device to perform operations comprising:
   receiving a user input for the creation of a user heart-beat profile associated with a user wearing a wearable computing device, wherein the user input further specifies a particular activity or time of day associated with the heart-beat profile;
   in response to the user input, monitoring real-time heart rate information over a period of time from a sensor component coupled to the wearable computing device;
   generating heart rate calibration information based on the monitoring;
   storing the heart rate calibration information in association with the particular activity or time of day;
   receiving, from the sensor component coupled to the wearable computing device, real-time heart rate information associated with the user;
   accessing the heart rate calibration information associated with the heart-beat profile;
   detecting an irregularity based on a comparison between the real-time heart rate information and the heart rate calibration information;
   based on the detected irregularity, accessing a contact information associated with a user profile; and
   transmitting a message based on the contact information.

18. The computer-readable device of claim 17, wherein:
   the user input further specifies a particular activity or time of day associated with the heart-beat profile, wherein the particular activity may be at least one of resting, exercising, working, or sleeping.

19. The computer-readable device of claim 17, the detecting an irregularity further comprising detecting a heart rate that is above a threshold heart rate for a particular time of the day.

20. The computer-readable device of claim 17, the operations further comprising:
   determining the user wearing the wearable computing device is performing a particular activity, wherein the accessed heart rate calibration information depends on the particular activity.

* * * * *